United States Patent [19]
Krüger et al.

[11] Patent Number: 6,008,257
[45] Date of Patent: Dec. 28, 1999

[54] HYDROXAMIC-ACID DERIVATIVES, METHOD OF PREPARING THEM AND THEIR USE AS FUNGICIDES

[75] Inventors: Bernd-Wieland Krüger, Bergisch Gladbach; Lutz Assmann, Eutin; Herbert Gayer, Monheim; Peter Gerdes, Aachen; Ulrich Heinemann, Leichlingen; Dietmar Kuhnt, Burscheid; Thomas Seitz, Langenfeld; Bernd Gallenkamp, Wuppertal; Ralf Tiemann; Gerd Hänssler, both of Leverkusen; Heinz-Wilhelm Dehne, Bonn; Stefan Dutzmann, Hilden, all of Germany

[73] Assignee: Bayer Aktiengesellschaft, Leverkusen, Germany

[21] Appl. No.: 08/916,045

[22] PCT Filed: Jan. 16, 1995

[86] PCT No.: PCT/EP95/00149

§ 371 Date: Jul. 22, 1996

§ 102(e) Date: Jul. 22, 1996

[87] PCT Pub. No.: WO95/20570

PCT Pub. Date: Aug. 3, 1995

Related U.S. Application Data

[63] Continuation of application No. 08/676,365, Jul. 22, 1996, abandoned.

[30] Foreign Application Priority Data

Jan. 28, 1994 [DE] Germany ............... 44 02 533

[51] Int. Cl.⁶ .................. A61K 31/16; C07C 239/18
[52] U.S. Cl. .................. 514/640; 562/623; 564/253; 564/256
[58] Field of Search ............ 514/640; 562/623; 564/253, 256

[56] References Cited

U.S. PATENT DOCUMENTS

| | | | |
|---|---|---|---|
| 5,395,854 | 3/1995 | Brand et al. | 514/619 |
| 5,516,804 | 5/1996 | Brand et al. | 514/619 |
| 5,523,454 | 6/1996 | Brand et al. | 558/408 |
| 5,677,347 | 10/1997 | Brand et al. | 514/620 |

FOREIGN PATENT DOCUMENTS

| | | |
|---|---|---|
| EP-A-463488 | 1/1992 | European Pat. Off. . |
| EP-A-579124 | 1/1994 | European Pat. Off. . |
| 4030038 | 3/1992 | Germany . |

*Primary Examiner*—Johann Richter
*Assistant Examiner*—John Dolan
*Attorney, Agent, or Firm*—Sprung Kramer Schaefer & Briscoe

[57] ABSTRACT

Hydroxamic derivatives of the formula (I):

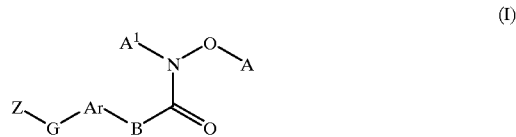

in which

A represents hydrogen or a grouping which can be readily eliminated;

$A^1$ represents hydrogen or alkyl;

Ar represents optionally substituted arylene or heteroarylene;

E represents a 1-alkene-1,1-diyl grouping which contains a radical $R^1$ in the 2-position, or represents a 2-aza-1-alkene-1,1-diyl grouping which contains a radical $R^2$ in the 2-position, or represents an optionally substituted imino grouping ("azamethylone", N—$R^3$);

G represents a bridge member as defined herein; and

Z represents in each case optionally substituted alkyl, alkenyl, alkinyl, cycloalkyl, aryl or heterocyclyl;

are useful as fungicides. Also disclosed is a process for preparing the compounds of formula (I).

8 Claims, No Drawings

HYDROXAMIC-ACID DERIVATIVES, METHOD OF PREPARING THEM AND THEIR USE AS FUNGICIDES

This application is a continuation of application Ser. No. 08/676,365, filed on Jul. 22, 1996 which is a 371 of PCT Application PCT/EP95/00149 filed on Jan. 16, 1995.

The invention relates to novel hydroxamic acid derivatives, to a process for preparing them and to their use as fungicides.

Certain hydroxamic acid derivatives, such as, for example, the compound N-hydroxy-α-hydroxyimino-furazan-ethanimidic acid, are already known (cf. Liebigs Ann. Chem. 1975, 1029–1050-cited in Chem. Abstracts 88:50732c). However, nothing has been disclosed with regard to the biological properties of such compounds.

The novel hydroxamic acid derivatives of the general formula (I) have now been found,

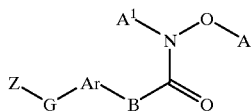

in which
- A represents hydrogen or a grouping which can readily be eliminated,
- $A^1$ represents hydrogen or alkyl,
- Ar represents in each case optionally substituted arylene or heteroarylene,
- E represents a 1-alkene-1,1-diyl grouping which contains a radical $R^1$ in the 2 position, or represents a 2-aza-1-alkene-1,1-diyl grouping which contains a radical $R^2$ in the 2 position, or represents an optionally substituted imino grouping ("azamethylene", N—$R^3$), where
- $R^1$ represents hydrogen, halogen or cyano, or in each case optionally substituted alkyl, alkoxy, alkylthio, alkylamino or dialkylamino,
- $R^2$ represents hydrogen, amino or cyano, or in each case optionally substituted alkyl, alkoxy, alkylamino or dialkylamino, and
- $R^3$ represents hydrogen or cyano, or in each case optionally substituted alkyl, alkenyl, alkinyl, cycloalkyl or cycloalkylalkyl,
- G represents oxygen, or alkanediyl, alkenediyl or alkinediyl which are in each case optionally substituted by halogen, hydroxyl, alkyl, halogenoalkyl or cycloalkyl, or one of the following groupings
—Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O=N—C(R$^4$)—, —N(R$^5$)—CQ—Q—, —CQ—N(R$^5$)—CQ—Q—, or —N(R$^5$)—CQ—Q—CH$_2$—,
where
- n represents the numbers 0, 1 or 2,
- Q represents oxygen or sulphur,
- $R^4$ represents hydrogen or cyano, or in each case optionally substituted alkyl, alkoxy, alkylthio, alkylamino, dialkylamino, or cycloalkyl, and
- $R^5$ represents hydrogen, hydroxyl or cyano, or in each case optionally substituted alkyl, alkoxy or cycloalkyl, and
- Z represents in each case optionally substituted alkyl, alkenyl, alkinyl, cycloalkyl, aryl or heterocyclyl.

In addition, it has been found that the novel hydroxamic acid derivatives of the general formula (I) are obtained if carboxylic acid derivatives of the general formula (II)

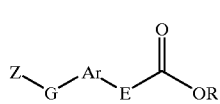

in which
Ar, E, G and Z have the abovementioned meaning, and
R represents hydrogen or alkyl,
are reacted with a hydroxylamine of the general formula (III)

in which
A and $A^1$ have the abovementioned meaning,
or with a hydrogen halide thereof
optionally in the presence of an acid acceptor and optionally in the presence of a diluent.

Finally, it has been found that the novel hydroxamic acid derivatives of the general formula (I) exhibit a very powerful fungicidal activity.

The compounds according to the invention may optionally be present as mixtures of different possible isomeric forms, in particular of E and Z isomers, optionally, however, also of tautomers. Both the E and the Z isomers, and also arbitrary mixtures of these isomers, as well as the possible tautomeric forms, are claimed.

The invention preferably relates to compounds of the formula (I) in which
- A represents hydrogen, alkyl having 1 to 8 carbon atoms which is optionally substituted by halogen, cyano, hydroxyl, $C_1$–$C_4$-alkoxy, $C_1$–$C_4$-alkoxy-$C_1$–$C_4$-alkoxy, N,N-di-($C_1$–$C_4$-alkyl)-amino, N-($C_1$–$C_4$-alkyl-carbonyl)-amino, N-($C_1$–$C_4$-alkyl)-N-($C_1$–$C_4$-alkyl-carbonyl)-amino, N-($C_1$–$C_4$-alkoxy-carbonyl)-amino or N-($C_1$–$C_4$-alkyl)-N-($C_1$–$C_4$-alkoxy-carbonyl)-amino, $C_1$–$C_4$-alkoxy-carbonyl, $C_1$–$C_4$-alkylamino-carbonyl or di-($C_1$–$C_4$-alkyl)-amino-carbonyl,
- $A^1$ represents hydrogen or alkyl having 1 to 6 carbon atoms,
- Ar represents in each case optionally substituted phenylene or naphthylene, or heteroarylene having 5 or 6 ring members, of which at least one represents oxygen, sulphur or nitrogen and optionally one or two additional members represent nitrogen, where the possible substituents are preferably selected from the following list: halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinloxy having in each case 2 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties, or in each case doubly linked alkylene or dioxyalkylene which have in each case 1 to 6 carbon atoms and which are in each case optionally substituted, once or more than once, identically or differently, by halogen and/or straight-chain or branched alkyl having 1 to 4 carbon atoms and/or straight-chain or branched halogenoalkyl having 1 to 4 carbon atoms and 1 to 9 identical or different halogen atoms, E represents one of the following groupings

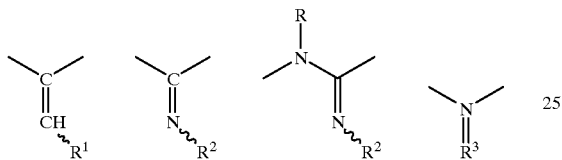

in which

R represents hydrogen or alkyl having 1 to 6 carbon atoms, $R^1$ represents hydrogen, halogen or cyano, or alkyl, alkoxy, alkylthio, alkylamino or dialkylamino which have in each case 1 to 6 carbon atoms in the alkyl radicals and which are in each case optionally substituted by halogen, cyano or $C_1$–$C_4$-alkoxy, $R^2$ represents hydrogen, amino or cyano, or alkyl, alkoxy, alkylamino or dialkylamino which have in each case 1 to 6 carbon atoms in the alkyl radicals and which are in each case optionally substituted by halogen, cyano or $C_1$–$C_4$-alkoxy, and $R^3$ represents hydrogen or cyano, or alkyl, alkenyl or alkinyl which have in each case up to 6 carbon atoms and which are in each case optionally substituted by halogen, cyano or $C_1$–$C_4$-alkoxy, or cycloalkyl or cycloalkylalkyl which have 3 to 6 carbon atoms in the cycloalkyl moieties and optionally 1 to 4 carbon atoms in the alkyl moiety and which are in each case optionally substituted by halogen, cyano, carboxyl, $C_1$–$C_4$-alkyl or $C_1$–$C_4$-alkoxy-carbonyl, G represents oxygen, alkanediyl, alkenediyl or alkinediyl which have in each case up to 4 carbon atoms and which are in each case optionally substituted by halogen, hydroxyl, $C_1$–$C_4$-alkyl, $C_1$–$C_4$-halogenoalkyl or $C_3$–$C_6$-cycloalkyl, or one of the following groupings —Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C($R^4$)=N—O—, —C($R^4$)=N—O—CH$_2$—, —N($R^5$)—, —CQ—N($R^5$)—, —N($R^5$)—CQ—, —Q—CQ—N($R^5$)—, —N=C($R^4$)—Q—CH$_2$—, —CH$_2$—O—N=C($R^4$)—, —N($R^5$)—CQ—Q—, —CQ—N($R^5$)—CQ—Q—, or —N($R^5$)—CQ—Q—CH$_2$—, where n represents the numbers 0, 1 or 2, Q represents oxygen or sulphur, $R^4$ represents hydrogen or cyano, or alkyl, alkoxy, alkylthio, alkylamino, or dialkylamino which have in each case 1 to 6 carbon atoms in the alkyl groups and which are optionally substituted by halogen, cyano or $C_1$–$C_4$-alkoxy, or cycloalkyl which has from 3 to 6 carbon atoms and which is in each case optionally substituted by halogen, cyano, carboxyl, $C_1$–$C_4$-alkyl or $C_1$–$C_4$-alkoxy-carbonyl, and $R^5$ represents hydrogen, hydroxyl or cyano, or alkyl which has 1 to 6 carbon atoms and which is optionally substituted by halogen, cyano or $C_1$–$C_4$-alkoxy, or cycloalkyl which has 3 to 6 carbon atoms and which is optionally substituted by halogen, cyano, carboxyl, $C_1$–$C_4$-alkyl or $C1$–$C4$-alkoxy-carbonyl, and Z represent alkyl which has 1 to 8 carbon atoms and which is optionally substituted by halogen, cyano, hydroxyl, amino, $C_1$–$C_4$-alkoxy, $C_1$–$C_4$-alkylthio, $C_1$–$C_4$-alkylsulphinyl or $C_1$–$C_4$-alkylsulphonyl (which are in each case optionally substituted by halogen), alkenyl or alkinyl which have in each case up to 8 carbon atoms and which are in each case optionally substituted by halogen, cycloalkyl which has 3 to 6 carbon atoms and which is in each case optionally substituted by halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl, in each case optionally substituted phenyl or naphthyl, or heterocyclyl having 3 to 7 ring members, of which at least one represents oxygen, sulphur or nitrogen and optionally one or two additional members represent nitrogen, where the possible substituents are preferably selected from the following list: halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case 1 to 6 carbon atoms, in each case straight-chain or branched alkenyl or alkenyloxy having in each case 2 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties, in each case doubly linked alkylene or dioxyalkylene which have in each case 1 to 6 carbon atoms and which are in each case optionally substituted, once or more than once, identically or differently, by halogen and/or straight-chain or branched alkyl having 1 to 4 carbon atoms and/or straight-chain or branched halogenoalkyl having 1 to 4 carbon atoms and 1 to 9 identical or different halogen atoms, cycloalkyl having 3 to 6 carbon atoms, heterocyclyl or heterocyclylmethyl having in each case 3 to 7 ring members, of which in each case 1 to 3 are identical or different hetero atoms—in particular nitrogen, oxygen and/or sulphur —, and also phenyl, phenoxy, benzyl, benzyloxy, phenylethyl or phenylethyloxy which are in each case optionally substituted in the phenyl moiety, once or more than once, identically or differently, by halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms.

In the definitions, the saturated or unsaturated hydrocarbon chains, such as alkyl, alkanediyl, alkenyl or alkinyl are, also when linked to heteroatoms, such as in alkoxy, alkylthio or alkylamino, in each case straight-chain or branched.

Halogen generally represents fluorine, chlorine, bromine or iodine, preferably fluorine, chlorine or bromine, in particular fluorine or chlorine.

The invention relates, in particular, to compounds of the formula (I), in which

A represents hydrogen, methyl, ethyl, n- or i-propyl, or n-, i-, s- or t-butyl which are optionally substituted by fluorine, chlorine, methoxy, ethoxy, n- or i-propoxy, methoxy-ethoxy, ethoxy-ethoxy, dimethylamino, diethylamino, acetylamino, propionylamino, N-methyl-acetylamino, N-ethyl-acetylamino, N-methyl-propionylamino, N-ethyl-propionylamino, methoxycarbonyl-amino, ethoxycarbonylamino, N-methyl-N-methoxycarbonylamino, N-ethyl-N-methoxycarbonylamino, N-methyl-N-ethoxycarbonylamino or N-ethyl-N-ethoxycarbonylamino, methoxycarbonyl, ethoxycarbonyl, methylaminocarbonyl, ethylaminocarbonyl, dimethylaminocarbonyl or diethylaminocarbonyl, $A^1$ represents hydrogen, methyl, ethyl, n- or i-propyl, or n-, i- or s-butyl, Ar represents in each case optionally substituted ortho-, meta- or para-phenylene, furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyrdinediyl (in particular pyridine-2,3-diyl), pyrimidinediyl, pyridazinediyl, pyrazinediyl, 1,3,4-triazinediyl or 1,2,3,-triazinediyl, where the possible substituents are selected, in particular, from the following list: fluorine, chlorine, cyano, methyl, ethyl, trifluoromethyl, methoxy, ethoxy, methylthio, methylsulphinyl or methylsulphonyl, E represents one of the following groupings

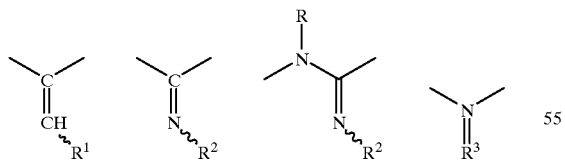

in which

R represents methyl, ethyl, n- or i-propyl, or n-, i- or s-butyl, $R^1$ represents hydrogen, fluorine, chlorine, bromine or cyano, or methyl, ethyl, propyl, methoxy, ethoxy, methylthio, ethylthio, methylamino, ethylamino or dimethylamino which are in each case optionally substituted by fluorine, chlorine, cyano, methoxy or ethoxy, $R^2$ represents hydrogen, amino or cyano, or methyl, ethyl, methoxy, ethoxy, methylamino, ethylamino or dimethylamino which are in each case optionally substituted by fluorine, chlorine, cyano, methoxy or ethoxy, and $R^3$ represents hydrogen or cyano, or methyl, ethyl, n- or i-propyl, or n-, i- or s-butyl which are in each case optionally substituted by fluorine, cyano, methoxy or ethoxy, represents allyl or propargyl, or represents cyclopropyl, cyclobutyl, cyclopentyl, cyclohexyl, cyclopropylmethyl, cyclobutylmethyl, cyclopentylmethyl or cyclohexylmethyl which are in each case optionally substituted by fluorine, chlorine, cyano, carboxyl, methyl, ethyl, n- or i-propyl, methoxycarbonyl or ethoxy-carbonyl, G represents oxygen, methylene, dimethylene (ethane-1, 2-diyl), ethene-1,2-diyl, ethine-1,2-diyl which are in each case optionally substituted by fluorine, chlorine, hydroxyl, methyl, ethyl, n- or i-propyl, trifluoromethyl, cyclopropyl, cyclobutyl, cyclopentyl or cyclohexyl, or one of the following groupings
—Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, or —N(R$^5$)—CQ—Q—CH$_2$—, where n represents the numbers 0, 1 or 2, Q represents oxygen or sulphur, $R^4$ represents hydrogen or cyano, or methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino which are optionally substituted by fluorine, chlorine, cyano, methoxy or ethoxy, or cyclopropyl, cyclobutyl, cyclopentyl or cyclohexyl which are in each case optionally substituted by fluorine, chlorine, cyano, carboxyl, methyl, ethyl, n- or i-propyl, methoxycarbonyl or ethoxy-carbonyl, and $R^5$ represents hydrogen, hydroxyl or cyano, or methyl, ethyl, n- or i-propyl, or n-, i-, s- or t-butyl which are in each case optionally substituted by fluorine, chlorine, cyano, methoxy or ethoxy, or cyclopropyl, cyclobutyl, cyclopentyl or cyclohexyl which are optionally substituted by fluorine, chlorine, cyano, carboxyl, methyl, ethyl, n- or i-propyl, methoxy-carbonyl or ethoxycarbonyl, and Z represents methyl, ethyl, n- or i-propyl, or n-, i-, s- or t-butyl which are optionally substituted by fluorine, chlorine, bromine, cyano, hydroxyl, amino, methoxy, ethoxy, methylthio, ethylthio, methylsulphinyl, ethylsulphinyl, methylsulphonyl or ethylsulphonyl (which are in each case optionally substituted by fluorine and/or chlorine), allyl, crotonyl, 1-methyl-allyl, propargyl or 1-methyl-propargyl which are in each case optionally substituted by fluorine, chlorine or bromine, cyclopropyl, cyclobutyl, cyclopentyl or cyclohexyl which are in each case optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl, or in each case optionally substituted phenyl, naphthyl, furyl, thienyl, oxazolyl, isoxazolyl, thiazolyl, isothiazolyl, oxadiazolyl, thiadiazolyl, pyridinyl, pyrimidinyl, pyridazinyl, pyrazinyl, 1,2,3-triazinyl, 1,2,4-triazinyl, 1,3,5-triazinyl, oxiranyl, oxetanyl, tetrahydrofuryl, perhydropyranyl, pyrrolidinyl, piperidinyl or morpholinyl, where the possible substituents are preferably selected from the following list: fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl; trimethylene (propane-1,3-diyl), methylenedioxy or ethylenedioxy which are in each case optionally substituted, once or more than once, identically or differently, by fluorine, chlorine, methyl, ethyl, or n- or i-propyl, cyclopropyl, cyclobutyl, cyclopentyl or cyclohexyl, and also phenyl, phenoxy, benzyl or benzyloxy which are in each case optionally substituted in the phenyl moiety, once or more than once, identically or differently, by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

A particularly preferred group of compounds according to the invention are those compounds of the formula (I) in which A represents hydrogen, $A^1$ represents hydrogen or methyl, Ar represents ortho-phenylene, pyridine-2,3diyl or thiophene-2,3-diyl, E represents one of the following groupings

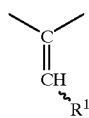 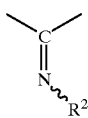

in which $R^1$ and $R^2$ in each case represent methoxy,

G represents oxygen, methylene or one of the following groupings

—CH$_2$—O—, —O—CH$_2$—, —S(O)$_n$—, —CH$_2$—S(O)$_n$—, —S(O)$_n$—CH$_2$—, —C(R$^4$)=N—O—, —O—N=C(R$^4$)—, —C(R$^4$)=N—O—CH$_2$—, —N(R$^5$)— or —CH$_2$—O—N=C(R$^4$)—, where n represents the numbers 0, 1 or 2, $R^4$ represents hydrogen, methyl or ethyl, and $R^5$ represents hydrogen, methyl or ethyl, and Z represents in each case optionally substituted phenyl, pyridinyl, pyrimidinyl, pyridazinyl, pyrazinyl, 1,2,3-triazinyl, 1,2,4-triazinyl or 1,3,5-triazinyl, where the possible substituents are preferably selected from the following list: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methoxycarbonyl, ethoxycarbonyl, methoxyiminomethyl, ethoxyiminomethyl, methoxyiminoethyl or ethoxyiminoethyl, or methylenedioxy or ethylenedioxy which are in each case optionally substituted, once or more than once, identically or differently, by fluorine, chlorine, methyl or ethyl, and also phenyl, phenoxy, benzyl or benzyloxy which are in each case optionally substituted in the phenyl moiety, once or more than once, identically or differently, by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

The above-listed general radical definitions, or those given in preference ranges, hold both for the end products of the formula (I) and also, in a corresponding manner, for the starting compounds and/or intermediates which are in each case required for preparation.

These radical definitions can be combined at will among one another, that is also between the given ranges of preferred compounds.

If, for example, methyl α-methoximino-α-(2-phenoxymethyl-phenyl)-acetate and hydroxylamine hydrochloride are used as starting compounds, the course of the reaction in the preparation process according to the invention can then be outlined by the following formula scheme:

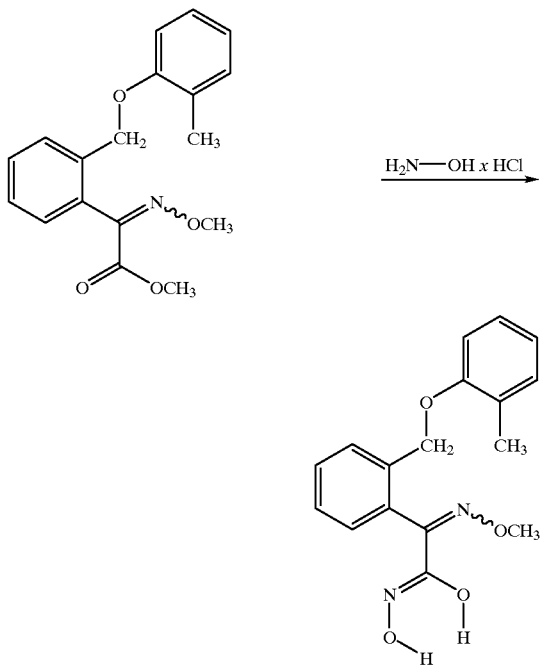

The carboxylic acid derivatives which are required as starting compounds for carrying out the process according to the invention are defined generally by the formula (II). In this formula (II), Ar, E, G and Z preferably, or in particular, have those meanings which have already been mentioned, in connection with the description of the compounds of the formula (I) according to the invention, as being preferred, or as being in particular preferred, for Ar, E, G and Z; R preferably represents alkyl having 1 to 4 carbon atoms, in particular methyl or ethyl.

The starting compounds of the formula (II) are known and/or can be prepared by methods which are known per se (cf. EP-A 178826, EP-A 242081, EP-A 382375, EP-A 493711).

The hydroxylamines which are also to be used as starting compounds are defined generally by the formula (III). In the formula (III), A preferably, or in particular, has that meaning which has already been mentioned, in connection with the description of the compounds of the formula (I) according to the invention, as being preferred, or as being in particular preferred, for A.

The starting compounds of the formula (III) are in a known manner organic synthesis chemicals.

The process according to the invention is preferably carried out in the presence of a suitable acid acceptor. All the customary inorganic or organic bases are suitable for use as such. These include, for example, alkaline earth metal or alkali metal hydrides, hydroxides, amides, alcoholates, acetates, carbonates or hydrogen carbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, N,N-dimethyl-benzylamine, pyridine, N-methylpiperidine, N,N-dimethylaminopyridine, diazabicyclooctane (DABCO), diazabicyclononene (DBN) or diazabicycloundecene (DBU).

Water and organic solvents are suitable for use as diluents for carrying out the process according to the invention. These solvents include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate, or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether or diethylene glycol monoethyl ether, and their mixtures with water, or pure water.

When carrying out the process according to the invention, the reaction temperatures can be varied within a relatively wide range. In general, temperatures of between −20° C. and +100° C., preferably temperatures of between 0° C. and 50° C., are employed.

In order to carry out the process according to the invention, from 1 to 5 mol, preferably from 1.0 to 2.5 mol, of hydroxylamine or hydroxylamine hydrogen halide and, where appropriate, from 1 to 10 mol, preferably from 1 to 5 mol, of acid acceptor are generally employed per mol of carboxylic acid derivative of the formula (II).

The conduct of the reaction, and working-up and isolation of the reaction products, are effected in accordance with known methods (cf. the preparation examples).

The active compounds according to the invention exhibit a powerful microbicidal effect and can be employed in practice for controlling undesirable microorganisms. The active compounds are suitable for use as phytoprotective agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubense;*
Plasmopara species, such as, for example, *Plasmopara viticola;*
Peronospora species, such as, for example, *Peronospora pisi* or *Peronospora brassicae;*
Erysiphe species such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *Pyrenophora graminea* (conidia form: Drechslera, synonym: Helminthosporium);
Cochliobolus species, such as, for example, *Cochliobolus sativus* (conidia form: Drechslera, synonym: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The good toleration, by plants, of the active compounds, at the concentrations required for controlling plant diseases, permits treatment of above-ground parts of plants, of vegetative propagation stock and seeds, and of the soil.

In this context, the active compounds according to the invention may be employed with a particularly high degree of success for controlling diseases in fruit and vegetable cultivation, such as, for example, against Phytophthora and Venturia species, or for controlling cereal diseases, such as, for example, against Erysiphe species, and also for controlling rice diseases, such as, for example, against *Pyricularia oryzae*.

Depending on their respective physical and/or chemical properties, the active compounds can be converted into customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can also be used, as such or in their formulations, mixed together with known fungicides, bactericides, acaricides, nematicides or insecticides in order, in this way, for example to broaden the spectrum of activity or to prevent the development of resistance. In many cases, synergistic effects appear under these circumstances.

Examples of suitable compounds for the mixtures are:

Fungicides

2-Aminobutane, 2-anilino-4-methyl-6-cyclopropyl-pyrimidine, 2'6'-dibromo-2-methyl-4'-trifluoromethoxy-4'-trifluoro-methyl-1,3-thizole-5-carboxanilide 2,6-dichloro-N-(4-trifluoromethylbenzyl)benzamide, (E)-2-methoxyimino-N-methyl-2-(2-phenoxyphenyl) acetamide, 8-hydroxyquinolinesulphate, methyl-(E)-2-{2-[6-(2-cyano-phenoxy)pyrimidin-4-yloxy]phenyl}-3-methoxyacrylate, methyl-(E)-methoximino [alpha-(o-tolyloxy)-o-tolyl] acetate, 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, Calcium polysulphide, captafol, captan, carbendazim, carboxin, chinomethionate (quinomethionate), chloroneb, chloropicrin, chlorothalonil, chlozolinate, cufraneb, cymoxanil, cyproconazole, cyprofuram, dichlorophen, diclobutrazol, diclofluanide, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper compounds, such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldthirocarbamate, nitrothal-isopropyl, nuarimol, ofurace, oxadixyl, oxamocarb, oxycarboxine, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolyfluanide, triadimefon, triadimenol, triazoxide, trichlamide, tricyclazole, tridemorph, triflumizole, triforine, triticonazole, validamycin A, vinclozolin, zineb, ziram Bactericides Bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides

Abamectin, abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyluthrine, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S. demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, permethrin, phenthoate, phorate, phosalone phosmet, phosphamdon, phoxim, pirimicarb, pirimiphos M, pirimiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen, quinalphos RH 5992 salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to have mixtures with other known active compounds, such as herbicides, or with fertilizers and growth regulators.

The active compounds can be used as such, in the form of their formulations or the use forms prepared therefrom, such as ready-to-use solutions, suspensions, wettable powders, pastes, soluble powders, dusting preparations and granules. They are used in the customary manner, for example by watering, spraying atomizing, scattering, dusting, foaming, brushing on and the like. It is furthermore possible to apply the active compounds by the ultra-low volume method or to inject the active compound preparation or the active compound itself into the soil. The seeds of plants can also be treated.

In the treatment of parts of plants, the active compound concentrations in the use forms can be varied over a relatively wide range: they are, in general between 1 and 0.0001% by weight, preferably between 0.5 and 0.001% by weight.

In the treatment of seed, amounts of active compound of from 0.001 to 50 g per kilogram of seed, preferably from 0.01 to 10 g, are generally required.

For the treatment of the soil, active compound concentrations of from 0.00001 to 0.1% by weight, preferably of from 0.0001 to 0.02% by weight, are required at the site of action.

PREPARATION EXAMPLES

Example 1

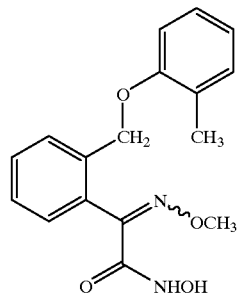

2.67 g (38.4 mmol) of hydroxylamine hydrochloride are initially introduced in 40 ml of methanol, and 6.0 g (19.2 mmol) of methyl α-methoximino-α-[2-(2-methyl-phenoxymethyl)-phenyl]-acetate are added in portions, at 10° C. 13.8 g of a 30% solution of sodium methoxide (76.8 mmol of NaOCH$_3$) are then added dropwise to the mixture, while cooling with ice and within the space of 15 minutes, and the reaction mixture is subsequently stirred, after removing the ice bath, at from 0° C. to 20° C. for 3 hours.

For the working-up, the mixture is stirred into dilute hydrochloric acid (prepared from 6 ml of conc. hydrochloric acid and 100 g of ice water), and the whole is then shaken with ethyl acetate; the organic phase is dried over sodium sulphate and filtered. The solvent is carefully distilled off from the filtrate in a water suction vacuum.

5.3 g (81% of theory) of α-methoximino-α-[2-(2-methyl-phenoxymethyl)-phenyl]-acetohydroxamic acid (92% pure by liquid chromatography) are obtained with a melting point of 65° C.

$^1$H NMR (D$_6$-dimethylsulphoxide, δ): 2.20, 3.88, 3.95, 6.8–7.55, 9.2 ppm

The compounds of the formula (I) which are listed in Table 1 below can, for example, also be prepared in analogy with Example 1 and in correspondence with the general description of the preparation process according to the invention.

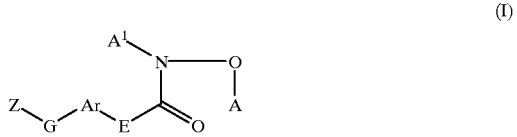

(I)

TABLE 1

Examples of the compounds of the formula (I)

| No. | Z | G | Ar | E | A | A¹ | Physical data |
|---|---|---|---|---|---|---|---|
| 2 | phenyl | H₃C-C(=N-O-CH₂-)- | 2,3-dimethylphenyl | CH₃O—N=C | H | H | (oil) |
| 3 | 3-methylphenyl | H₃C-C(=N-O-CH₂-)- | 2,3-dimethylphenyl | CH₃O—N=C | H | H | (oil) |
| 4 | 4-(5-methyl-1,2,4-thiadiazol-3-yl)pyridine | O | 2,3-dimethylphenyl | CH₃O—CH=C | H | H | |
| 5 | 3-(5-methyl-1,2,4-thiadiazol-3-yl)pyridine | O | 2,3-dimethylphenyl | CH₃O—CH=C | H | H | |
| 6 | 2-(5-methyl-1,2,4-thiadiazol-3-yl)thiophene | O | 2,3-dimethylphenyl | CH₃O—CH=C | H | H | |

TABLE 1-continued
Examples of the compounds of the formula (I)
| No. | Z | G | Ar | E | A | A¹ | Physical data |
|-----|---|---|----|---|---|----|----|
| 7 |  | O |  | CH₃O—CH=C | H | H | |
| 8 |  | O |  | CH₃O—CH=C | H | H | |
| 9 |  | O |  | CH₃O—CH=C | H | H | |
| 10 |  | O | | CH₃O—CH=C | H | H | |

TABLE 1-continued
Examples of the compounds of the formula (I)
| No. | Z | G | Ar | E | A | A¹ | Physical data |
|---|---|---|---|---|---|---|---|
| 11 | 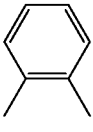 | O |  | CH₃O—N=C | H | H | |
| 12 | 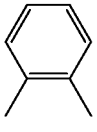 | O |  | CH₃O—N=C | H | H | |
| 13 | 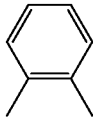 | O |  | CH₃O—N=C | H | H | |
| 14 | 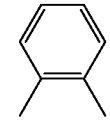 | O |  | CH₃O—N=C | H | H | |
| 15 | 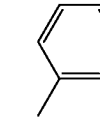 | O |  | CH₃O—N=C | H | H | |

TABLE 1-continued

Examples of the compounds of the formula (I)

| No. | Z | G | Ar | E | A | A₁ | Physical data |
|---|---|---|---|---|---|---|---|
| 16 | 4-pyridyl-(5-methyl-1,2,4-thiadiazol-3-yl) | SO₂CH₂ | 2,3-dimethylphenyl | CH₃O—N=C< | H | H | |
| 17 | 3-chloro-4-methyl-(trifluoromethoxy)phenyl | —OCH₂— | 2,3-dimethylphenyl | CH₃O—N=C< | H | H | |
| 18 | 3-(trifluoromethyl)phenyl | —OCH₂— | 2,3-dimethylphenyl | CH₃O—N=C< | H | H | ¹H NMR (DMSO, δ): 3.84; 3.87; 5.01; 5.05; 7.03–7.54; 9.2; 11.2 ppm |
| 19 | 2,4-dimethylphenyl | —OCH₂— | 2,3-dimethylphenyl | CH₃O—N=C< | H | H | ¹H NMR (DMSO, δ): 2.16; 2.18; 3.86; 3.88; 4.85; 4.91; 6.62–7.54; 8.94; 9.2; 11.2 ppm |
| 20 | 2,5-dimethylphenyl | —OCH₂— | 2,3-dimethylphenyl | CH₃O—N=C< | H | H | ¹H NMR (DMSO, δ): 1.99–2.23; 3.87–3.92; 4.87; 4.93; 6.47–7.54; 9.08; 11.2 ppm |

TABLE 1-continued
Examples of the compounds of the formula (I)
| No. | Z | G | Ar | E | A | A¹ | Physical data |
|---|---|---|---|---|---|---|---|
| 21 | 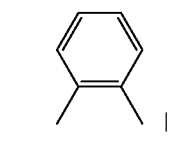 | —OCH₂— | 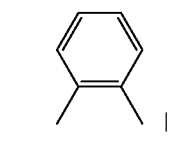 | CH₃O—N=C< | H | H | |
| 22 | 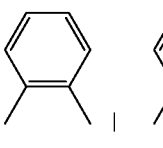 | —OCH₂— | 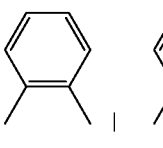 | CH₃O—N=C< | H | H | |
| 23 | 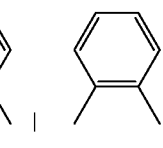 | —OCH₂— | 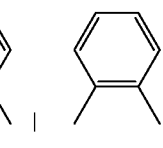 | CH₃O—N=C< | H | H | |
| 24 | 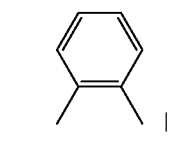 | —OCH₂— | 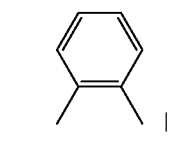 | CH₃O—N=C< | H | H | |
| 25 | 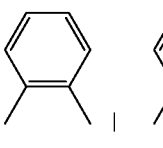 | —OCH₂— | 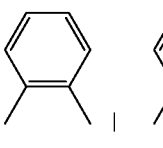 | CH₃O—N=C< | H | H | |
| 26 | 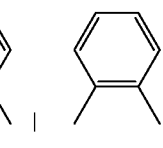 | —OCH₂— | 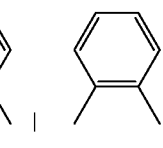 | CH₃O—N=C< | H | H | |

TABLE 1-continued

Examples of the compounds of the formula (I)

| No. | Z | G | Ar | E | A | A¹ | Physical data |
|-----|---|---|----|----|---|----|---------------|
| 27 | 2,4-Cl₂-phenyl (with CH₃) | —OCH₂— | phenyl | CH₃O—N=C< | H | H | |
| 28 | 3-CH₃-phenyl | O | phenyl | CH₃O—N=C< | H | H | |
| 29 | 2-CH₃-phenyl | O | pyridyl (N) | CH₃O—N=C< | H | H | |
| 30 | 2-CH₃-phenyl | O | thienyl (S) | CH₃O—N=C< | H | H | |
| 31 | phenyl | NC–C(=N–O–CH₂–) | phenyl | CH₃O—N=C< | H | H | |
| 32 | 2,3-(CH₃)₂-phenyl | NC–C(=N–O–CH₂–) | phenyl | CH₃O—N=C< | H | H | |
| 33 | 3-CH₃-phenyl | NC–C(=N–O–CH₂–) | phenyl | CH₃O—N=C< | H | H | |

TABLE 1-continued
Examples of the compounds of the formula (I)
| No. | Z | G | Ar | E | A | A$^1$ | Physical data |
|---|---|---|---|---|---|---|---|
| 34 |  |  |  | 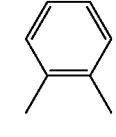 | H | H | |
| 35 | 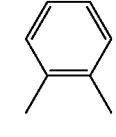 |  |  |  | H | H | |
| 36 |  |  | 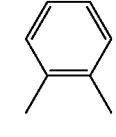 |  | H | H | |
| 37 |  |  |  |  | H | H | |
| 38 |  | 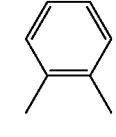 |  |  | H | H | |
| 39 |  |  |  | 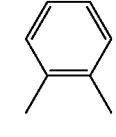 | H | H | |
| 40 | 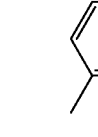 |  |  |  | H | H | |

TABLE 1-continued
Examples of the compounds of the formula (I)
| No. | Z | G | Ar | E | A | A¹ | Physical data |
|---|---|---|---|---|---|---|---|
| 41 | 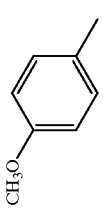 | 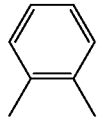 | 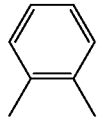 | CH₃O—N=C< | H | H | |
| 42 | 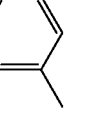 | 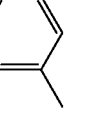 | 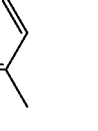 | CH₃O—N=C< | H | H | |
| 43 | 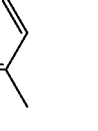 | 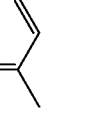 | 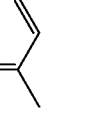 | CH₃O—N=C< | H | H | |
| 44 | 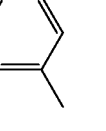 | 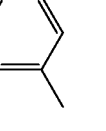 | 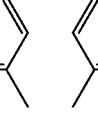 | CH₃O—N=C< | H | H | |
| 45 | 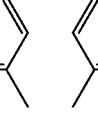 |  | | CH₃O—N=C< | H | H | |
| 46 | | | | CH₃O—N=C< | H | H | |
| 47 | | | | CH₃O—N=C< | H | H | |

TABLE 1-continued
Examples of the compounds of the formula (I)
| No. | Z | G | Ar | E | A | A¹ | Physical data |
|---|---|---|---|---|---|---|---|
| 48 | 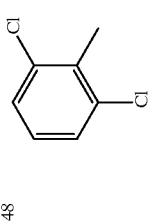 | 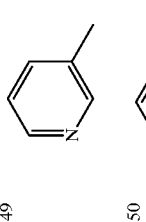 | 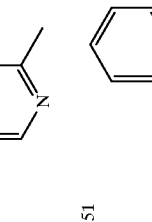 | CH₃O—N=C< | H | H | |
| 49 | 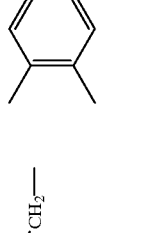 | 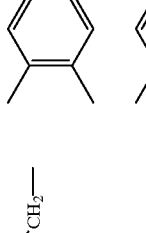 | 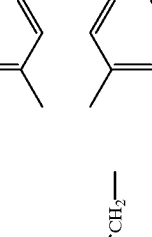 | CH₃O—N=C< | H | H | |
| 50 | 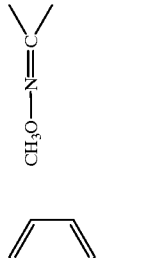 | 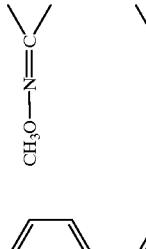 | 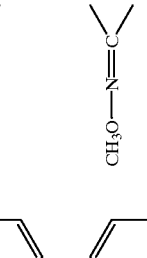 | CH₃O—N=C< | H | H | |
| 51 |  |  |  | CH₃O—N=C< | H | H | ¹H NMR (DMSO, δ): 2.256 (3H); 3.861 (3H); 5.104 (2H); 7.172/7.196 (1H); 7.234–7.502 (3H); 7.622/7.648/7.674 (1H); 7.760/7.786 (1H); 7.927–7.957 (2H); 9.146/9.151 (1H); 11.166/11.497 (1H) ppm |
| 52 | 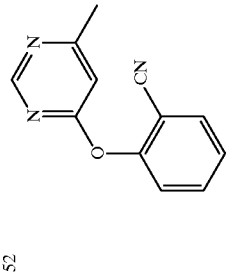 | O | | CH₃O—CH=C< | H | H | |

TABLE 1-continued
Examples of the compounds of the formula (I)
| No. | Z | G | Ar | E | A | A¹ | Physical data |
|---|---|---|---|---|---|---|---|
| 53 | 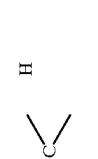 | O | 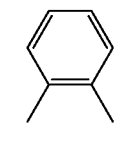 | CH₃O—CH= |  | H | |
| 54 | 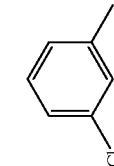 | —OCH₂— |  | CH₃O—N=C |  | H | ¹H NMR (DMSO, δ): 3.86; 5.0; 6.92–7.33; 9.2 ppm |
| 55 | 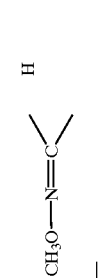 | —OCH₂— | 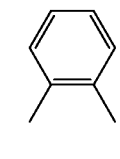 | CH₃O—N=C | 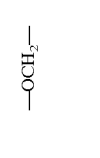 | H | ¹H NMR (CDCl₃, δ): 3.93; 5.03; 6.80–7.62 ppm |
| 56 | 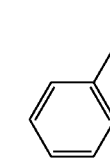 | —OCH₂— |  | CH₃O—N=C |  | H | ¹H NMR (DMSO, δ): 3.88; 4.93; 6.74–6.79; 7.19–7.52 ppm |
| 57 |  | —OCH₂— | 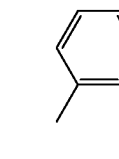 | CH₃O—N=C |  | H | ¹H NMR (DMSO, δ): 2.2; 3.87; 4.98; 6.81–7.56; 9.2; 11.2 ppm |

TABLE 1-continued
Examples of the compounds of the formula (I)
| No. | Z | G | Ar | E | A | A¹ | Physical data |
|---|---|---|---|---|---|---|---|
| 58 | 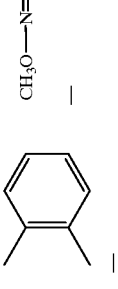 | —O— | 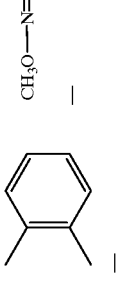 | CH₃O—N=C< | H | H | ¹H NMR (CDCl₃, δ): 3.9 (s, 3H); 5.4 (m, 1H) |
| 59 | 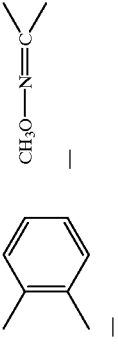 | —OCH₂— | 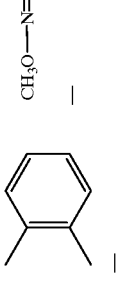 | CH₃O—N=C< | H | H | ¹H NMR (DMSO, δ): 3.9; 5.0; 6.8–7.6; 9.2 ppm |
| 60 | 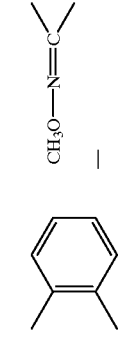 | —OCH₂— | 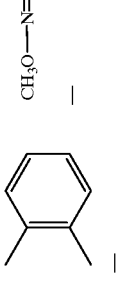 | CH₃O—N=C< | H | H | ¹H NMR (CDCl₃, δ): 3.9; 5.1–5,18; 6.93–8.25; 9.2 ppm |
| 61 | 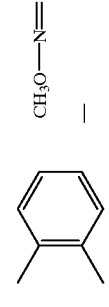 | —OCH₂— | 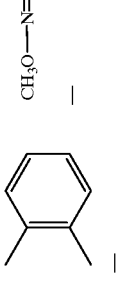 | CH₃O—N=C< | H | H | ¹H NMR (DMSO, δ): 3.88; 3.91; 4.95; 5.0; 6.85–7.56; 9.25; 11.3 ppm |
| 62 | 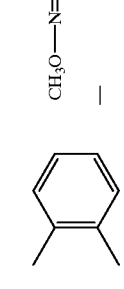 | —OCH₂— | 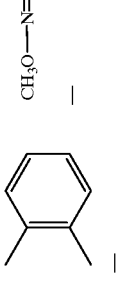 | CH₃O—N=C< | H | H | ¹H NMR (DMSO, δ): 1.1; 3.3; 3.9; 4.9; 6.8–7.5; 9.2 ppm |
| 63 |  | —OCH₂— | 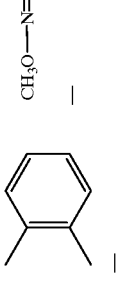 | CH₃O—N=C< | H | H | ¹H NMR (DMSO, δ): 1.1; 2.6; 3.9; 4.9; 6.7–7.5; 9.2 ppm |

TABLE 1-continued

Examples of the compounds of the formula (I)

| No. | Z | G | Ar | E | A | A¹ | Physical data |
|---|---|---|---|---|---|---|---|
| 64 | | —OCH₂— | | CH₃O—N=C | | H | ¹H NMR (DMSO, δ): 2.2; 3.9; 4.9; 6.7–7.5; 9.2 ppm |
| 65 | | —OCH₂— | | CH₃O—N=C | | H | ¹H NMR (DMSO, δ): 2.04–2.21; 3.86; 3.89; 4.86; 4.92; 6.74–7.52; 9.2; 11.2 ppm |
| 66 | | —OCH₂— | | CH₃O—N=C | | H | ¹H NMR (DMSO, δ): 3.75–3.91; 4.86; 4.94; 6.8–7.53; 9.2; 11.2 ppm |
| 67 | | | | CH₃O—N=C | | H | (oil) |
| 68 | | O | | CH₃O—N=C | | H | (oil) |
| 69 | | —OCH₂— | | CH₃O—N=C | | H | ¹H NMR (DMSO, δ): 1.06–1.19; 2.23; 2.51–2.62; 3.90; 4.93; 6.66–7.54; 9.20; 11.20 ppm |
| 70 | | —OCH₂— | | CH₃O—N=C | | H | ¹H NMR (DMSO, δ): 3.88–3.91; 2.20; 3.21–3.43; 4.90–5.02; 5.77–5.92; 6.54–7.52; 9.17; 11.25 ppm. |

TABLE 1-continued
Examples of the compounds of the formula (I)
| No. | Z | G | Ar | E | A | A¹ | Physical data |
|---|---|---|---|---|---|---|---|
| 71 | 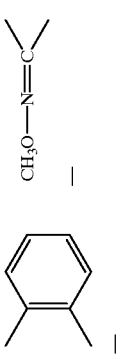 | —OCH₂— | | CH₃O—N=C | H | H | ¹H NMR (DMSO, δ): 3.87; 5.04; 5.09; 7.21–7.99; 9.23; 11.25 ppm. |
| 72 | | —OCH₂— | | CH₃O—N=C | H | H | ¹H NMR (DMSO, δ): 3.91; 4.92; 6.85–7.52; 8.8 ppm. |
| 73 | 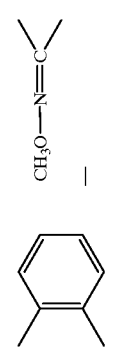 | —OCH₂— | | CH₃O—N=C | H | H | ¹H NMR (DMSO, δ): 3.91; 3.96; 4.97; 6.84–8.40 ppm. |
| 74 | 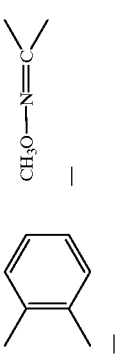 | —OCH₂— | | CH₃O—N=C | H | H | ¹H NMR (DMSO, δ): 3.84–3.90; 4.94; 4.99; 6.93–7.53; 8.14; 9.21; 11.20 ppm. |
| 75 | | —OCH₂— | | CH₃O—N=C | H | CH₃ | ¹H NMR (DMSO, δ): 3.47; 3.97; 4.98; 6.82–7.57 ppm |
| 76 | 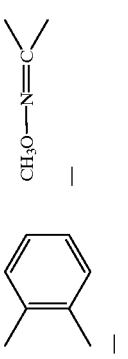 | 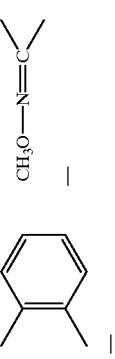 | | CH₃O—N=C | CH₂C₆H₅ | H | ¹H NMR (DMSO, δ): 2.21; 3.91; 4.95; 5.13; 7.18–7.86; 9.03 ppm. |

TABLE 1-continued

Examples of the compounds of the formula (I)

| No. | Z | G | Ar | E | A | A¹ | Physical data |
|---|---|---|---|---|---|---|---|
| 77 | 2,3-dimethylphenyl (CH₃) | —OCH₂— | 2,3-dimethylphenyl | CH₃O—N=C< | —CH₂-(2-chlorothiazol-5-yl) | H | ¹H NMR (DMSO, δ): 2.22; 3.95; 4.95; 6.78–7.55; 9.11 ppm. |

Application Examples

Example A
Pyricularia Test (Rice)/Protective
Solvent: 12.5 parts by weight of acetone
Emulsifier: 0.3 part by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, the compound according to Preparation Example 1, for example, exhibited a degree of effectiveness of 100% at an active compound concentration of 0.025%.

Example B
Pyricularia Test (Rice)/Systemic
Solvent: 12.5 parts by weight of acetone
Emulsifier: 0.3 part by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, the compound according to Preparation Example 1, for example, exhibited a degree of effectiveness of 67% when used at the rate of 100 mg per 100 cm².

Example C
Phytophthora Test (Tomato)/Protective
Solvent: 12.5 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation until dripping wet. After the spray coating has dried on, the plants are inoculated with an aqueous spore suspension of *Phytophthora infestans*.

The plants are placed in an incubation cabin at 100% relative atmospheric humidity and at about 20° C.

Evaluation is carried out 3 days after the inoculation.

In this test, the compound according to Preparation Example 1, for example, exhibited a degree of effectiveness of 67% at an active compound concentration of 0.025%.

Example D
Erysiphe Test (Barley)/Protective
Solvent: 12.5 parts by weight of N-methyl-pyrrolidone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compound according to Preparation Example 1, for example, exhibited a degree of effectiveness of 89% at an active compound concentration of 0.025%.

Example E
Venturia Test (Apple)/Protective
Solvent: 12.5 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism *Venturia inaequalis* and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compound according to preparation example 1, for example, exhibited a degree of effectiveness of 100% at an active compound concentration of 0.025%

We claim:

1. A hydroxamic derivative of the formula (I):

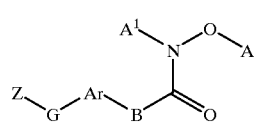

(I)

in which
 A represents hydrogen;
 $A^1$ represents hydrogen or alkyl;
 Ar represents optionally substituted arylene;
 E represents a 1-alkene-1,1-diyl group which contains a radical $R^1$ in the 2-position, or represents a 2-aza-1-alkene-1,1-diyl group which contains a radical $R^2$ in the 2-position, or represents an optionally substituted imino group N—$R^3$;
where
 $R^1$ represents hydrogen, halogen, optionally substituted alkyl, optionally substituted alkoxy, optionally substituted alkylthio, optionally substituted alkylamino or optionally substituted dialkylamino;
 $R^2$ represents hydrogen, amino, optionally substituted alkyl, optionally substituted alkoxy, optionally substituted alkylamino or optionally substituted dialkylamino; and R³ represents hydrogen, optionally substituted alkyl, optionally substituted alkenyl, optionally substituted alkinyl, optionally substituted cycloalkyl or optionally substituted cycloalkylalkyl;

G represents oxygen, or represents optionally substituted alkanediyl, optionally substituted alkenediyl or optionally substituted alkinediyl, wherein the optional substituents are selected from the group consisting of halogen, hydroxyl, alkyl, halogenoalkyl and cycloalkyl, or represents a member selected from the group consisting of:

—CH₂—Q—,   —Q—CH₂—,   —S(O)ₙ—, —CH₂S(O)ₙ—, —CQ—, —S(O)ₙ—CH₂—, —C(R⁴)=N—O—, —C(R⁴)=N—O—CH₂—, —N(R⁵)—, —CQ—N(R⁵)—, —N(R⁵)—CQ—, —N=C(R⁴)—Q—CH₂—, and —CH₂—O—N=C(R⁴)— where n represents the numbers 0, 1 or 2;

Q represents oxygen or sulphur;

R⁴ represents hydrogen, optionally substituted optionally substituted alkoxy, optionally substituted alkylthio, optionally substituted alkylamino, optionally substituted dialkylamino, or optionally substituted cycloalkyl; and R⁵ represents hydrogen, hydroxyl, optionally substituted alkyl, optionally substituted alkoxy or optionally substituted cycloalkyl; and Z represents optionally substituted alkyl, optionally substituted alkenyl, optionally substituted alkinyl, optionally substituted cycloalkyl, or optionally substituted aryl.

2. A hydroxamic acid derivative of the formula (I) according to claim 1, in which A represents hydrogen;

A¹ represents hydrogen or alkyl having 1 to 6 carbon atoms;

Ar represents optionally substituted phenylene or optionally substituted naphthylene, wherein the substituents on said phenylene or naphthylene are selected from the group consisting of halogen, nitro, amino, hydroxyl, formyl, straight-chain or branched alkyl having 1 to 6 carbon atoms, straight-cain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched alkenyl having 2 to 6 carbon atoms, straight-chain or branched alkenyloxy having 2 to 6 carbon atoms, straight-chain or branched alkinyloxy having 2 to 6 carbon atoms, straight-chain or branched halogenoalkyl having 1 to 6 carbon atoms and 1 to 13 identical or different halogen atoms, straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, straight-chain or branched halogenoalkenyl having 2 to 6 carbon atoms and 1 to 13 identical or different halogen atoms, straight-chain or branched halogenoalkenyloxy having 2 to 6 carbon atoms and 1 to 13 identical or different halogen atoms, straight-chain or branched alkylamino having 1 to 6 carbon atoms, straight-chain or branched dialkylamino having 1 to 6 carbon atoms in each alkyl moiety, straight-chain or branched alkylcarbonyl having 1 to 6 carbon atoms in the alkyl moiety, straight-chain or branched alkylcarbonyloxy having 1 to 6 carbon atoms in the alkyl moiety, straight-chain or branched alkylsulphonyloxy having 1 to 6 carbon atoms in the alkyl moiety, straight-chain or branched hydroxyiminoalkyl having 1 to 6 carbon atoms in the alkyl moiety, straight-chain or branched alkoxyiminoalkyl having 1 to 6 carbon atoms in the alkoxy and alkyl moieties, optionally substituted alkylene having 1 to 6 carbon atoms or optionally substituted dioxyalkylene having 1 to 6 carbon atoms, wherein the substituents for said alkylene or dioxyalkylene are one or more substituents independently selected from the group consisting of halogen, straight-chain or branched alkyl having 1 to 4 carbon atoms and straight-chain or branched halogenoalkyl having 1 to 4 carbon atoms and 1 to 9 identical or different halogen atoms;

E represents one of the following groups:

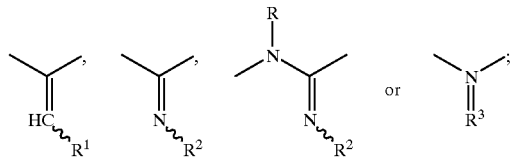

in which

R represents hydrogen or alkyl having 1 to 6 carbon atoms;

R¹ represents hydrogen, halogen, optionally substituted alkyl having 1 to 6 carbon atoms, optionally substituted alkoxy having 1 to 6 carbon atoms, optionally substituted alkylthio having 1 to 6 carbon atoms, optionally substituted alkylamino having 1 to 6 carbon atoms or optionally substituted dialkylamino having 1 to 6 carbon atoms in each alkyl radical, wherein the substituents are in each case selected from the group consisting of halogen, and C₁–C₄-alkoxy;

R² represents hydrogen, amino, optionally substituted alkyl, alkoxy having 1 to 6 carbon atoms, optionally substituted alkylamino having 1 to 6 carbon atoms or optionally substituted dialkylamino having 1 to 6 carbon atoms in each alkyl radical, wherein the substituents are in each case selected from the group consisting of halogen, and C₁–C₄-alkoxy; and R³ represents hydrogen, optionally substituted alkyl having 1 to 6 carbon atoms, optionally substituted alkenyl having 2 to 6 carbon atoms or optionally substituted alkinyl having 2 to 6 carbon atoms, wherein the substituents on alkyl, alkenyl and alkinyl are selected from the group consisting of halogen, and C₁–C₄-alkoxy, or represents optionally substituted cycloalkyl having 3 to 6 carbon atoms or optionally substituted cycloalkylalkyl which has 3 to 6 carbon atoms in the cycloalkyl moiety, wherein the substituents on cycloalkyl and cycloalkylalkyl are selected from the group consisting of halogen, and C₁–C₄-alkyl;

G represents oxygen, or represents optionally substituted alkanediyl having 1 to 4 carbon atoms, optionally substituted alkenediyl having 2 to 4 carbon atoms or optionally substituted alkinediyl having 2 to 4 carbon atoms, wherein the substituents on alkanediyl, alkenediyl and alkinediyl are selected from the group consisting of halogen, hydroxyl, $C_1$–$C_4$-alkyl, $C_1$–$C_4$-halogenoalkyl and $C_3$–$C_6$-cycloalkyl, or represents a member selected from the group consisting of:

—$CH_2$—Q—,  —Q—$CH_2$—,  —S(O)$_n$—,
—$CH_2$—S(O)$_n$—, —CQ—, —S(O)$_n$—$CH_2$—,
—C($R^4$)=N—O—, —C($R^4$)=N—O—$CH_2$—,
—N($R^5$)—, —CQ—N($R^5$)—, —N($R^5$)—CQ—,
—N=C($R^4$)—Q—$CH_2$—, and —$CH_2$—O=N—C($R^4$)—;

where n represents the numbers 0, 1 or 2;

Q represents oxygen or sulphur;

$R^4$ represents hydrogen, optionally substituted alkyl having 1 to 6 carbon atoms, optionally substituted alkoxy having 1 to 6 carbon atoms, optionally substituted alkylthio having 1 to 6 carbon atoms, optionally substituted alkylamino having 1 to 6 carbon atoms, or optionally substituted dialkylamino having 1 to 6 carbon atoms in each alkyl group, wherein the substituents are in each case selected from the group consisting of halogen, and $C_1$–$C_4$-alkoxy, or represents optionally substituted cycloalkyl which has from 3 to 6 carbon atoms, wherein the substituents on cycloalkyl are selected from the group consisting of halogen, and $C_1$–$C_4$-alkyl; and $R^5$ represents hydrogen, hydroxyl, optionally substituted alkyl having 1 to 6 carbon atoms, wherein the substituents on alkyl are selected from the group consisting of halogen, and $C_1$–$C_4$-alkoxy, or represents optionally substituted cycloalkyl having 3 to 6 carbon atoms, wherein the substituents on cycloalkyl are selected from the group consisting of halogen, and $C_1$–$C_4$-alkyl; and Z represents optionally substituted alkyl having 1 to 8 carbon atoms, wherein the substituents on alkyl are selected from the group consisting of halogen, hydroxyl, amino, optionally halogen substituted $C_1$–$C_4$-alkoxy, optionally halogen substituted $C_1$–$C_4$-alkylthio, optionally halogen substituted $C_1$–$C_4$-alkylsulphinyl and optionally halogen substituted $C_1$–$C_4$-alkylsulphonyl, or Z represents optionally halogen substituted alkenyl having 2 to 8 carbon atoms or optionally halogen substituted alkinyl having 2 to 8 carbon atoms, or Z represents optionally substituted cycloalkyl having 3 to 6 carbon atoms, wherein the substituents on cycloalkyl are selected from the group consisting of halogen, $C_1$–$C_4$-alkyl, and optionally substituted phenyl, wherein the substituents on phenyl are, in turn, selected from the group consisting of halogen, $C_1$–$C_4$-alkyl, $C_1$–$C_4$-halogenoalkyl, $C_1$–$C_4$-alkoxy and $C_1$–$C_4$-halogenoalkoxy, or Z represents optionally substituted phenyl, optionally substituted naphthyl, wherein the substituents on phenyl, or naphthyl are selected from the group consisting of halogen, nitro, amino, hydroxyl, formyl, straight-chain or branched alkyl having 1 to 6 carbon atoms, straight-chain or branched alkoxy having 1 to 6 carbon atoms, straight-chain or branched alkylthio having 1 to 6 carbon atoms, straight-chain or branched alkylsulphinyl having 1 to 6 carbon atoms, straight-chain or branched alkylsulphonyl having 1 to 6 carbon atoms, straight-chain or branched alkenyl having 2 to 6 carbon atoms, straight-chain or branched alkenyloxy having 2 to 6 carbon atoms, straight-chain or branched halogenoalkyl having 1 to 6 carbon atoms and 1 to 13 identical or different halogen atoms, straight-cain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, straight-chain or branched halogenoalkylsulphinyl having 1 to 6 carbon atoms and 1 to 13 identical or different halogen atoms, straight-chain or branched halogenoalkylsulphonyl having 1 to 6 carbon atoms and 1 to 13 identical or different halogen atoms, straight-chain or branched halogenoalkenyl having 2 to 6 carbon atoms and 1 to 13 identical or different halogen atoms, straight-chain or branched halogenoalkenyloxy having 2 to 6 carbon atoms and 1 to 13 identical or different halogen atoms, straight-chain or branched alkylamino having 1 to 6 carbon atoms in the alkyl moiety, straight-chain or branched dialkylamino having 1 to 6 carbon atoms in each alkyl moiety, straight-chain or branched alkylcarbonyl having 1 to 6 carbon atoms in the alkyl moiety, straight-chain or branched alkylcarbonyloxy having 1 to 6 carbon atoms in the alkyl moiety, straight-chain or branched alkylsulphonyloxy having 1 to 6 carbon atoms in the alkyl moiety, straight-chain or branched hydroxyiminoalkyl having 1 to 6 carbon atoms in the alkyl moiety, straight-chain or branched alkoxyiminoalkyl having 1 to 6 carbon atoms in the alkoxy and alkyl moieties, optionally substituted alkylene having 1 to 6 carbon atoms or optionally substituted dioxyalkylene having 1 to 6 carbon atoms, wherein the substituents on alkylene and dioxyalkylene are one or more substituents independently selected from the group consisting of halogen, straight-chain or branched alkyl having 1 to 4 carbon atoms and straight-chain or branched halogenoalkyl having 1 to 4 carbon atoms and 1 to 9 identical or different halogen atoms, cycloalkyl having 3 to 6 carbon atoms, and phenyl, phenoxy, benzyl, benzyloxy, phenylethyl or phenylethyloxy, each of which is, in turn, optionally substituted in the phenyl moiety, once or more than once, identically or differently, by halogen, straight-chain or branched alkyl having 1 to 4 carbon atoms, straight-chain or branched halogenoalkyl having 1 to 4 carbon atoms and 1 to 9 identical or different halogen atoms or straight-chain or branched halogenoalkoxy having 1 to 4 carbon atoms and 1 to 9 identical or different halogen atoms.

3. A hydroxamic acid derivative of the formula (I) according to claim 1, in which A represents hydrogen;

$A^1$ represents hydrogen, methyl, ethyl, n-propyl, i-propyl, n-butyl, i-butyl or s-butyl;

Ar represents orthophenylene, metaphenylene, or paraphenylene, each of which is optionally substituted by one or more substituents independently selected from the group consisting of fluorine, chlorine, cyano, methyl, ethyl, trifluoromethyl, methoxy, ethoxy, methylthio, methylsulphinyl or methylsulphonyl;

E represents one of the following groups:

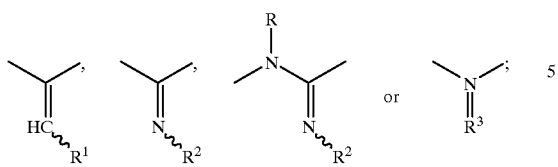

in which
R represents methyl, ethyl, n-propyl, i-propyl, n-butyl, i-butyl or s-butyl;

R¹ represents hydrogen, fluorine, chlorine, or bromine or represents methyl, ethyl, propyl, methoxy, ethoxy, methylthio, ethylthio, methylamino, ethylamino or dimethylamino, each of which is optionally substituted by fluorine, chlorine, methoxy or ethoxy;

R² represents hydrogen, or amino or represents methyl, ethyl, methoxy, ethoxy, methylamino, ethylamino or dimethylamino, each of which is optionally substituted by fluorine, chlorine, methoxy or ethoxy; and R³ represents hydrogen or represents methyl, ethyl, n-propyl, i-propyl, n-butyl, i-butyl or s-butyl, each of which is optionally substituted by fluorine, methoxy or ethoxy, or represents allyl or propargyl, or represents cyclopropyl, cyclobutyl, cyclopentyl, cyclohexyl, cyclopropylmethyl, cyclobutylmethyl, cyclopentylmethyl or cyclohoxylmethyl, each of which is optionally substituted by fluorine, chlorine, methyl, ethyl, n-propyl, or i-propyl;

G represents oxygen, or represents methylene, dimethylene, ethene-1,2-diyl, ethine-1,2-diyl, each of which are optionally substituted by fluorine, chlorine, hydroxyl, methyl, ethyl, n-propyl, i-propyl, trifluoromethyl, cyclopropyl, cyclobutyl, cyclopentyl or cyclohexyl, or represents a member selected from the group consisting of:
—CH₂—Q—, —Q—CH₂—, —S(O)ₙ—, —CH₂—S(O)ₙ—, —CQ—, —S(O)ₙ—CH₂—, —C(R⁴)=N—O—, —C(R⁴)=N—O—CH₂—, —N(R⁵)—, —CQ—N(R⁵)—, —N(R⁵)—CQ—, —N=C(R⁴)—Q—CH₂—, and —CH₂—O—N=C(R⁴)—;

where
n represents the numbers 0, 1 or 2;
Q represents oxygen or sulphur;
R⁴ represents hydrogen or represents methyl, ethyl, n-propyl, i-propyl, n-butyl, i-butyl, s-butyl, methoxy, ethoxy, propoxy, butoxy, methylthio, ethylthio, propylthio, butylthio, methylamino, ethylamino, propylamino, dimethylamino or diethylamino, each of which is optionally substituted by fluorine, chlorine, methoxy or ethoxy, or represents cyclopropyl, cyclobutyl, cyclopentyl or cyclohexyl, each of which is optionally substituted by fluorine, chlorine, methyl, ethyl, n-propyl or i-propyl; and
R⁵ represents hydrogen, hydroxyl or represents methyl, ethyl, n-propyl, i-propyl, n-propyl, i-propyl, s-propyl or t-butyl, each of which is optionally substituted by fluorine, chlorine, methoxy or ethoxy, or represents cyclopropyl, cyclobutyl, cyclopentyl or cyclohexyl, each of which is optionally substituted by fluorine, chlorine, methyl, ethyl, n-propyl, or i-propyl; and
Z represents methyl, ethyl, n-propyl, i-propyl, n-butyl, i-butyl, s-butyl or t-butyl, each of which is optionally substituted by fluorine, chlorine, bromine, hydroxyl, amino, or methoxy, ethoxy, methylthio, ethylthio, methylsulphinyl, ethylsulphinyl, methylsulphonyl or ethylsulphonyl, each of which are, in turn, optionally substituted by fluorine and/or chlorine, or Z represents allyl, crotonyl, 1-methylallyl, propargyl or 1-methylpropargyl, each of which is optionally substituted by fluorine, chlorine or bromine, or Z represents cyclopropyl, cyclobutyl, cyclopentyl or cyclohexyl, each of which is optionally substituted by fluorine, chlorine, bromine, methyl, ethyl, n-propyl, i-propyl or phenyl, which is, in turn, optionally substituted by fluorine, chlorine, bromine, methyl, ethyl, n-propyl, i-propyl, n-butyl, i-butyl, s-butyl, t-butyl, trifluoromethyl, methoxy, ethoxy, n-propoxy, i-propoxy, difluoromethoxy or trifluoromethoxy, or Z represents phenyl, or naphthyl, each of which is optionally substituted by one or more substituents independently selected from the group consisting of fluorine, chlorine, bromine, nitro, amino, hydroxyl, formyl, methyl, ethyl, n-propyl, i-propyl, n-butyl, i-butyl, s-butyl, t-butyl, methoxy, ethoxy, n-propoxy, i-propoxy, methylthio, ethylthio, n-propylthio, i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, methylamino, ethylamino, n-propylamino, i-propylamino, dimethylamino, diethylamino, acetyl, propionyl, acetyloxy, methylsulphonyloxy, ethylsulphonyloxy, hydroxyiminomethyl, hydroxyiminoethyl, methoxyiminomethyl, ethoxyiminomethyl, methoxyiminoethyl, ethoxyiminoethyl, or trimethylene, methylenedioxy or ethylenedioxy, which are, in turn, optionally substituted, once or more than once, identically or differently, by fluorine, chlorine, methyl, ethyl, or n-propyl or i-propyl, cyclopropyl, cyclobutyl, cyclopentyl or cyclohexyl, and phenyl, phenoxy, benzyl or benzyloxy, each of which, in turn, is optionally substituted in the phenyl moiety, once or more than once, identically or differently, by fluorine, chlorine, bromine, methyl, ethyl, n-propyl, i-propyl, n-butyl, i-butyl, s-butyl, t-butyl, trifluoromethyl, methoxy, ethoxy, n-propoxy, i-propoxy, difluoromethoxy or trifluoromethoxy.

4. A hydroxamic acid derivative of the formula (I) according to claim 1, in which
A represents hydrogen;
A¹ represents hydrogen or methyl;
Ar represents orthophenylene;
E represents one of the following groups:

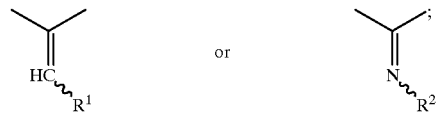

in which
R¹ and R² in each case represent methoxy;
G represents oxygen, methylene or a member selected from the group consisting of:
—CH₂—O—, —O—CH₂—, —S(O)ₙ—, —CH₂S(O)ₙ—, —S(O)ₙ—CH₂—, —C(R⁴)=N—O—, —O—N=C(R⁴)—, —C(R⁴)=N—O—CH₂—, N(R⁶)— and —CH₂—O—N=C(R⁴)—;

where n represents the numbers 0, 1 or 2;

R⁴ represents hydrogen, methyl or ethyl; and

R⁵ represents hydrogen, methyl or ethyl; and

Z represents phenyl, which is optionally substituted by one or more substituents independently selected from the group consisting of fluorine, chlorine, bromine, methyl, ethyl, n-propyl, i-propyl, n-butyl, i-butyl, s-butyl, t-butyl, methoxy, ethoxy, n-propoxy, i-propoxy, methylthio, ethylthio, n-propylthio, i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, methoxyiminomethyl, ethoxyiminomethyl, methoxyiminoethyl, ethoxyiminoethyl, or methylenedioxy or ethylenedioxy, which, in turn, are optionally substituted, once or more than once, identically or differently, by fluorine, chlorine, methyl or ethyl, and phenyl, phenoxy, benzyl or benzyloxy, which, in turn, are optionally substituted in the phenyl moiety, once or more than once, identically or differently, by fluorine, chlorine, bromine, methyl, ethyl, n-propyl, i-propyl, n-butyl, i-butyl, s-butyl, t-butyl, trifluoromethyl, methoxy, ethoxy, n-propoxy, i-propoxy, difluoromethoxy or trifluoromethoxy.

5. Process for preparing hydroxamic acid derivatives of the general formula (I) according to claim 1, characterized in that carboxylic acid derivatives of the general formula (II)

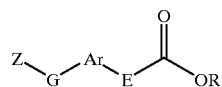
(II)

in which

Ar, E, G and Z have the meaning stated in claim 1, and

R represents hydrogen or alkyl, are reacted with a hydroxylamine of the general formula (III)

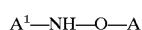
A¹—NH—O—A    (III)

in which

A and A¹ have the meaning stated in claim 1, or with a hydrogen halide thereof optionally in the presence of an acid acceptor and optionally in the presence of a diluent.

6. A pesticidal composition comprising a pesticidally effective amount of a hydroxamic acid derivative of the formula (I) according to claim 1 and a diluent.

7. A method of combating pests comprising applying a pesticidally effective amount of a hydroxamic acid derivative of the formula (I) according to claim 1 to the pests or their habitat or to an area from which one desires to exclude such pests.

8. The method according to claim 7, wherein the pests are fungi, and the method comprises applying a fungicidally effective amount of said hydroxamic acid derivative of the formula (I) to said fungi, their habitat or to an area from which one desires to exclude such fungi.

* * * * *